United States Patent
Nocker et al.

(10) Patent No.: US 10,882,811 B2
(45) Date of Patent: Jan. 5, 2021

(54) SYNTHESIS OF LYSINE ACETYLSALICYLATE GLYCINE PARTICLES

(71) Applicant: ASPIAIR GMBH, Gemünden (DE)

(72) Inventors: Karlheinz Nocker, Reiskirchen (DE); Ralf Zuhse, Berlin (DE); Dmytro Ostrovskyi, Luckenwalde (DE)

(73) Assignee: ASPIAIR GMBH, Gemünden (DE)

( * ) Notice: Subject to any disclaimer, the term of this patent is extended or adjusted under 35 U.S.C. 154(b) by 0 days.

(21) Appl. No.: 16/472,726

(22) PCT Filed: Dec. 22, 2017

(86) PCT No.: PCT/EP2017/084369
§ 371 (c)(1),
(2) Date: Jun. 21, 2019

(87) PCT Pub. No.: WO2018/115434
PCT Pub. Date: Jun. 28, 2018

(65) Prior Publication Data
US 2019/0322610 A1    Oct. 24, 2019

(30) Foreign Application Priority Data

Dec. 23, 2016 (EP) .................................... 16206723

(51) Int. Cl.
*C07C 51/00* (2006.01)

(52) U.S. Cl.
CPC .................... *C07C 51/00* (2013.01)

(58) Field of Classification Search
CPC .................................................... C07C 51/00
(Continued)

(56) References Cited

U.S. PATENT DOCUMENTS

| 2,101,867 | A | 12/1937 | Miller et al. |
| 3,392,195 | A | 7/1968 | Galat et al. |
| 4,265,888 | A | 5/1981 | Kagitani et al. |
| 4,446,132 | A | 5/1984 | Bender et al. |
| 4,988,683 | A | 1/1991 | Corbiere |
| 6,773,724 | B2 | 8/2004 | Gerhard et al. |

(Continued)

FOREIGN PATENT DOCUMENTS

| ES | 385222 | 4/1973 |
| FR | 1295304 A | 6/1962 |

(Continued)

OTHER PUBLICATIONS

International Search Report of International Application No. PCT/EP2017/084369, dated Mar. 21, 2018, 2 pages.

(Continued)

*Primary Examiner* — Deborah D Carr
(74) *Attorney, Agent, or Firm* — Hoxie & Associates LLC

(57) ABSTRACT

The invention relates to a method for the production of acetylsalicylic acid lysinate, optionally lysine acetylsalicylate.glycine, comprising the following steps: a) providing a solution of acetylsalicylic acid in ethanol; b) providing an aqueous solution of lysine; c) combining the solutions of step a) and b) to form a mixture; d) optionally stirring the mixture; e) adding acetone to the mixture; f) incubating the mixture, to allow the formation of a acetylsalicylic acid lysinate product; g) isolating the acetylsalicylic acid lysinate product; wherein acetylsalicylic acid is used in excess compared to lysine and wherein no seed crystals are added to the mixture; and optionally the following further steps: h) providing a recrystallized glycine; wherein the glycine has been recrystallized with the following steps: h1) dissolving glycine in water; h2) adding acetone to the glycine solution; h3) stirring the mixture until a precipitate is obtained; i) combining the recrystallized glycine of step h) with the acetylsalicylic acid lysinate product of step g) to obtain lysine acetylsalicylate.glycine (LASAG) particles.

18 Claims, 9 Drawing Sheets

(58) Field of Classification Search
USPC .......................................................... 562/448
See application file for complete search history.

(56) References Cited

U.S. PATENT DOCUMENTS

| | | | |
|---|---|---|---|
| 8,063,243 | B2 | 11/2011 | Franckowiak et al. |
| 9,492,413 | B2 | 11/2016 | Ludwig |
| 9,745,246 | B2 | 8/2017 | Arnal |
| 2005/0171070 | A1 | 8/2005 | Ecker et al. |
| 2006/0166901 | A1 | 7/2006 | Yu et al. |
| 2009/0306024 | A1 | 12/2009 | Ledwoch et al. |

FOREIGN PATENT DOCUMENTS

| | | | | |
|---|---|---|---|---|
| FR | | 2973370 B1 | 10/2012 | |
| FR | | 2992641 | 1/2014 | |
| WO | | WO-0205782 A2 * | 1/2002 | ........... A61K 31/616 |
| WO | | WO-2009089822 A2 * | 7/2009 | ............. A61K 9/088 |
| WO | | WO 2011/039432 | 4/2011 | |
| WO | | WO-2011039432 A1 * | 4/2011 | ............. C07C 67/28 |
| WO | | WO 2017/109037 | 6/2017 | |
| WO | | WO-2017109037 A1 * | 6/2017 | ............. A61K 45/06 |

OTHER PUBLICATIONS

English Machine Translation of Description and Claims of Application No. FR1295304A, Obtained via E-spacenet, Date Obtained: Jun. 9, 2020, 4 pages.

English Machine Translation of Abstract, Description and Claims of Application No. FR2973370B1, Obtained via E-spacenet, Date Obtained: Jun. 8, 2020, 9 pages.

* cited by examiner

Figure 3a cont.

UV-Detector (237nm)

| Pk # | Name | Retention Time | Area | Area Percent |
|---|---|---|---|---|
| 1 | | 1.94 | 27679 | 0.16 |
| 2 | | 2.06 | 30992 | 0.18 |
| 3 | Acetylsalicylsäure | 4.29 | 16596680 | 98.25 |
| 4 | Salicylsäure | 6.21 | 113098 | 0.67 |
| 5 | | 11.21 | 114332 | 0.68 |
| 6 | | 15.39 | 5284 | 0.03 |
| 7 | | 16.57 | 4962 | 0.03 |

Figure 3b cont.

| UV-Detector (237nm) | | | | |
|---|---|---|---|---|
| Pk # | Name | Retention Time | Area | Area Percent |
| 1 | | 1.94 | 20722 | 0.13 |
| 2 | | 2.14 | 1527 | 0.01 |
| 3 | Acetylsalicylsäure | 4.31 | 15958524 | 97.96 |
| 4 | Salicylsäure | 6.18 | 306278 | 1.88 |
| 5 | | 11.28 | 3511 | 0.02 |

Figure 4 cont.

UV-Detector (237nm)

| Pk # | Name | Retention Time | Area | Area Percent |
|---|---|---|---|---|
| 1 |  | 1.96 | 17947 | 0.08 |
| 2 | Acetylsalicylsäure | 4.58 | 22461357 | 99.45 |
| 3 |  | 6.15 | 8370 | 0.04 |
| 4 |  | 6.61 | 89268 | 0.40 |
| 5 |  | 12.36 | 8455 | 0.04 |

US 10,882,811 B2

SYNTHESIS OF LYSINE ACETYLSALICYLATE GLYCINE PARTICLES

CROSS REFERENCE TO RELATED APPLICATIONS

This application is a United States application under 35 U.S.C. § 371 claiming benefit of International Application No. PCT/EP2017/084369, filed on Dec. 22, 2017, which claims the benefit of European Application No. 16206723.5 filed on Dec. 23, 2016, the contents of each of which are incorporated herein by reference in their entireties.

BACKGROUND OF THE INVENTION

Acetylsalicylic acid, known under its trade name Aspirin, has been used in therapy for over 100 years. In particular, o-acetylsalicylic acid is widely used as analgesic, antipyretic or antirheumatic agent, as well as a non-steroid anti-inflammatory agent in arthritis, neuralgia or myalgia.

Unfortunately, acetylsalicylic acid has a limited solubility in water, which limits its resorption speed and with that the potential application forms. It was found that some acetylsalicylic acid salts show a significantly improved resorption speed. In particular, salts of acetylsalicylic acid with basic amino acids, especially lysine, show a highly-improved resorption speed.

The commonly used salt of acetyl salicylic acid in this context is therefore acetylsalicylic acid lysinate (also referred to as lysine acetylsalicylate). The salt has been known for over 60 years. It has been utilized in several pharmaceutical compositions and applications. An advantage of acetylsalicylic acid lysinate is a high tolerance in oral applications, as well as an increased speed of the raise of the blood level compared to acetylsalicylic acid alone.

A further important salt is lysine acetylsalicylate.glycine (LASAG; also referred to as D,L-lysine acetylsalicylate.glycine), which shows further beneficial properties. By controlling the particle size of LASAG it is possible to control important parameters, such as dissolution speed (also referred to as dissolution rate).

The synthesis of acetylsalicylic acid lysinate and LASAG was the subject of several optimization attempts. Unfortunately, the different synthesis methods have some minor or major drawbacks. The generally used synthesis method today involves an excess of lysine and the use of acetylsalicylic acid lysinate seed crystals. A drawback of the use seed crystals is a greater risk for contamination of the final product.

Some other methods for the synthesis of acetylsalicylic acid lysinate do not require seed crystals, but suffer from a low yield compared to methods utilizing seed crystals (e.g. about 70% yield compared to 90 to 95% yield).

Therefore, there is a need for a new and improved synthesis method, which does not require seed crystals, but retains a high yield of acetylsalicylic acid lysinate. Furthermore, there is a need for a LASAG synthesis, which allows for the easy preparation of LASAG particles with defined and small particle sizes.

SUMMARY OF THE INVENTION

The invention relates to a method for the production of acetylsalicylic acid lysinate, optionally lysine acetylsalicylate.glycine, comprising the following steps:

a) providing a solution of acetylsalicylic acid in ethanol;
b) providing an aqueous solution of lysine;
c) combining the solutions of step a) and b) to form a mixture;
d) optionally stirring the mixture;
e) adding acetone to the mixture;
f) incubating the mixture, to allow the formation of a acetylsalicylic acid lysinate product;
g) isolating the acetylsalicylic acid lysinate product;
wherein acetylsalicylic acid is used in excess compared to lysine and
wherein no seed crystals are added to the mixture; and optionally
h) providing a recrystallized glycine; wherein the glycine has been recrystallized with the following steps:
　h1) dissolving glycine in water;
　h2) adding acetone to the glycine solution;
　h3) stirring the mixture until a precipitate is obtained;
i) combining the recrystallized glycine of step h) with the acetylsalicylic acid lysinate product of step g) to obtain lysine acetylsalicylate.glycine (LASAG) particles.

In a preferred embodiment of the invention, the obtained particles—and in particular the LASAG particles obtained in step i)—have a median particle size of less than 40 µm and 90% of the particles have a particle size of 110 µm or less.

DETAILED DESCRIPTION OF THE INVENTION

Figure 1:
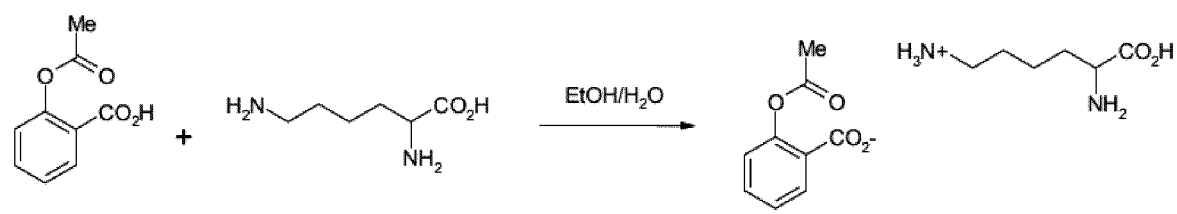
FIG. 1: Reaction scheme for the production of acetylsalicylic lysinate.

The inventors found an improved method for the production of acetylsalicylic acid lysinate, which provides very high yields (90%) without the need for seed crystals. The method additionally provides a significantly reduced product formation time. An optional modification of this method allows for the production of lysine acetylsalicylate.glycine with defined and small particle size.

Accordingly, in a first aspect, the invention relates to a method for the production of acetylsalicylic acid lysinate, optionally lysine acetylsalicylate.glycine, comprising the following steps:

a) providing a solution of acetylsalicylic acid in ethanol;
b) providing an aqueous solution of lysine;
c) combining the solutions of step a) and b) to form a mixture;
d) optionally stirring the mixture;
e) adding acetone to the mixture;
f) incubating the mixture, to allow the formation of a acetylsalicylic acid lysinate product;
g) isolating the acetylsalicylic acid lysinate product;
wherein acetylsalicylic acid is used in excess compared to lysine and
wherein no seed crystals are added to the mixture;

and optionally the following further steps:
h) providing a recrystallized glycine; wherein the glycine has been recrystallized with the following steps:
   h1) dissolving glycine in water;
   h2) adding acetone to the glycine solution;
   h3) stirring the mixture until a precipitate is obtained;
i) combining the recrystallized glycine of step h) with the acetylsalicylic acid lysinate product of step g) to obtain lysine acetylsalicylate.glycine (LASAG) particles.

The method can comprise up to two optional steps:
g1) washing the isolated product, and/or
j) sterilizing the isolated product.

In a second aspect, the invention relates to an acetylsalicylic acid lysinate, and optionally a lysine acetylsalicylate.glycine (LASAG), obtainable by the above described method(s) according to the first aspect of the invention.

The method is particularly suitable for producing LASAG particles with a defined particle size. The term particle size in the context of the present invention refers to the particle diameter as measured by laser diffraction; for instance, using the Mastersizer 3000 laser diffractometer (Malvern Instruments) equipped with a dry powder module. The terms particle size and particle diameter may thus be used synonymously herein. Where referring to the particle size measurements, all percentages provided herein (such as 'at least 90% of the particles have a particle size of . . . ') are to be understood as volume-percentages.

Preferably, the LASAG particles obtained in step i) have a median particle size of less than 100 μm, preferably less than 80 μm, more preferably less than 50 μm, particularly preferably less than 40 μm and especially preferably less than 30 μm. In a further preferred embodiment, at least 90% of the LASAG particles obtained in step i) have a particle size of less than 200 μm, preferably less than 175 μm, more preferably less than 150 μm, even more preferably less than 130 μm, particularly preferably less than 120 μm and especially preferably less than 110 μm. In a yet further preferred embodiment, not more than 10% of the LASAG particles obtained in step i) have a particle size of less than 1 μm, preferably less than 2 μm, more preferably less than 3 μm.

In a specific embodiment of the invention, the LASAG particles obtained in step i) have a median particle size of less than 50 μm and at least 90% of the particles have a particle size of 150 μm or less. In a preferred embodiment the LASAG particles obtained in step i) have a median particle size of less than 40 μm and at least 90% of the particles have a particle size of 130 μm or less. In a more preferred embodiment the LASAG particles obtained in step i) have a median particle size of less than 30 μm and at least 90% of the particles have a particle size of 110 μm or less. For instance, in one of the further preferred embodiments, the LASAG particles obtained in step i) have a median particle size of less than 30 μm, at least 90% of the particles have a particle size of 110 μm or less, and not more than 10% of the particles have a particle size of 3 μm or less.

Acetylsalicylic acid, within the context of the present invention, preferably refers to o-acetylsalicylic acid.

Steps a) and b), the provision of acetylsalicylic acid in ethanol and the provision of an aqueous solution of lysine, might be performed at any temperature. The solutions might be treated in any way required or desired. In a preferred embodiment, the at least one solution of steps a) and/or b) have been pretreated in order to sterilize the solutions before use. In one embodiment of the invention at least one of the solutions of step a) and/or b) has been sterile filtered.

In some embodiments of the invention, the solutions of steps a) and/or b) might contain further additives, such as for example glycine.

The provided solutions might be pretreated before use. Pretreatment comprises any treatment before the use of the solutions in the method. Some pretreatments involve that a solution was heated, cooled or frozen prior to use in the method. In some embodiments, at least one of the solutions has been heated or cooled. In other embodiments, at least one of the solutions has been irradiated. In other embodiments, several different pretreatments have been combined on at least one solution.

The solutions of steps a) and b) should comprise sufficiently pure compounds and be based on pharmaceutical grade solvents. The compounds acetylsalicylic acid and lysine are preferably at least substantially pure, more preferably at least of pharmaceutical grade purity, most preferably essentially free of impurities.

The solutions of step a) and/or b) may comprise similar concentrations of the compounds or comprise to different concentrations of the compounds. In one preferred embodiment of the invention, the solution of step a) preferably comprises about 8 to 12% (w/v) of acetylsalicylic acid. In a preferred embodiment of the invention the solution comprises about 9 to 11% (w/v) of acetylsalicylic acid. Most preferably the solution comprises about 9 to 10% (w/v) of acetylsalicylic acid.

The solution comprising lysine is preferably of higher concentration than the solution comprising acetylsalicylic acid. In one embodiment of the invention, the aqueous solution comprising lysine of step b) comprises about 25 to 40% (w/v) lysine. In a preferred embodiment of the invention the aqueous solution of step b) comprises about 30 to 35% (w/v) lysine. Most preferably, the aqueous solution of step b) comprises about 32 to 33% (w/v) lysine.

Preferably, lysine is used in the form of the free base. Even if it is possible to use lysine in salt form, e.g. as lysine hydrochloride, it is preferred to use lysine in the form of lysine monohydrate.

It is not relevant, which stereoisomer of lysine is used. It is also possible to use a mixture of stereo-isomers. In one embodiment of the invention, D-lysine is used. In a preferred embodiment, L-lysine is used. In an alternative embodiment of the invention D,L-Lysine is used.

It is important for the method that the molar amount of acetylsalicylic acid exceeds the molar amount of lysine in the final mixture. It is preferred that a small excess of acetylsalicylic acid to lysine is used. In one embodiment of the invention, acetylsalicylic acid is used in at least 1.05-fold molar excess compared to lysine. Preferably, acetylsalicylic acid is used in at least 1.07-fold molar excess and more preferably, acetylsalicylic acid is used in at least 1.1-fold molar excess.

In one particular embodiment of the invention, acetylsalicylic acid and lysine are used at about a 1 to 0.95 molar ratio. In a more preferred embodiment of the invention acetylsalicylic acid and lysine are used at about a 1 to 0.90 molar ratio.

In some embodiments, any of the solutions of step a) or b) might additionally comprise glycine. For example, the solution comprising lysine of step b) may additionally comprise glycine. In an alternative embodiment, glycine is provided as a separate solution. If glycine is added in a separate solution, it is preferred that glycine is provided in a solution of about 75 to 85% (v/v) ethanol. In one embodiment, the amount of glycine in the final dry product is in the range from 8 to 12 wt.-%, or about 10% (w/w).

If a glycine solution is added, the solution is preferably added at the same time the solutions of step a) and b) are combined or with or shortly after the addition of acetone.

In some embodiments, if glycine is desired in the final product, i.e. the solid form of acetylsalicylic acid lysinate, the glycine may also be added at a later stage and in solid form; for instance, the recrystallized glycine as described above in optional step h).

It is generally preferred, that the volume of the ethanol solution of step a) exceeds the volume of the aqueous solution of step b). Preferably, the volume of the ethanol solution of step a) is at least about 2 times, preferably at least about 3 times, more preferably at about 4 times as large as the volume of the aqueous solution of step b).

Steps a) and b) might be performed in any order.

Step c) combining the solutions to form a mixture can be performed in any suitable way. Preferably, the solutions are combined slowly, while optionally stirring the forming mixture. Ideally the mixture will start to crystallize during the mixing process. In a preferred embodiment, the solutions are combined by adding the solution of step b) to the solution of step a), while the solution and forming mixture is stirred. Preferably, the solutions are combined within less than one hour, more preferably within less than 30 minutes, more preferably within less than 15 minutes, even more preferably within less than 10 minutes, most preferably within less than 5 minutes.

The mixture then may optionally be stirred for a defined period of time. Preferably, the mixture is stored for less than 24 hours, preferably the mixture is stirred for less than 12 hours, more preferably for less than 6 hours, even more preferably the mixture is stirred for less than 3 hours, more preferably less than 1 hour. In a further preferred embodiment, the mixture is stirred for less than 15 minutes.

After combining the solutions in step c) and optional stirring, acetone is added to the mixture. Preferably, the amount of acetone added is about the same volume as the present mixture, more preferably a slightly lower amount is added. In one embodiment, the volume of acetone added corresponds to about 1 to 1.2 times the volume of the ethanol solution of step a). In a preferred embodiment, the volume of acetone corresponds to about 1.05 to 1.15 times the volume of the ethanol solution of step a). Most preferably, the volume of acetone corresponds to about 1.1 times the volume of the ethanol solution of step a).

The addition of acetone should result in a supersaturated mixture, which leads to improved and faster crystallization with higher yields. Accordingly, the amount of acetone used should be sufficient to ensure supersaturation of the mixture.

In a preferred embodiment of the invention the acetone is added after crystallization has started, i.e. after initial precipitate has formed. Usually the first precipitate should form without the use of seed crystals within 10 minutes or less. In several embodiments of the invention, the first precipitate forms within five minutes.

The main advantage of the method according to the invention is that no seed crystals are necessary to achieve high purity of the product after a short product formation time, even in industrial scale. Other methods used in industrial scale require the use of seed crystals or in other cases result in significantly lower yields than the method of the invention.

After the addition of acetone, the mixture should be allowed to incubate to allow formation of acetylsalicylic acid lysinate crystals. A further advantage of the method is that no long incubation time is needed for the method of the invention. High yields of product are achieved in less than three hours of incubation time. The mixture may or may not be stirred during incubation and crystal formation. In a preferred embodiment of the invention, the mixture is stirred during incubation.

The mixture might be incubated as long as necessary. However, the advantage of the invention is the short incubation time. In one embodiment of the invention, the mixture is incubated for about three hours or less, preferably for about two hours or less, more preferably for about one hour or less. In a most preferred embodiment the mixture is incubated for about 30 minutes.

In a particular preferred embodiment of the invention, the mixture is incubated for about one hour less and stirred during incubation.

After incubation the precipitated product should be isolated. Any method, which allows separation of the precipitated product from the liquid solution is suitable. Preferably, the product is isolated by filtration or centrifugation. In the most preferred embodiment of the invention the product is isolated by filtration.

As already stated above, the product may optionally be washed in an optional step g1) to remove impurities. Preferably the product is washed with acetone. More preferably, the product is washed multiple times with acetone. In one embodiment of the invention, the isolated product is washed at least one time, preferably at least two times, more preferably at least three times.

After isolating and washing the product, the product may optionally be dried. Within the context of the invention the term drying refers to the removal of solvent residues, preferably the removal of excess water, ethanol and acetone. The solvents may be removed by any suitable method, however, drying at room temperature over time or lyophilizing the product is preferred. As used herein, the term room temperature refers to a range of 20±5° C.

In a particular embodiment of the invention, the method includes the addition of glycine to obtain lysine acetylsalicylate.glycine. In this case, the method involves proving glycine, preferably recrystallized glycine.

In one embodiment of the invention, glycine is recrystallized by dissolving glycine in water. Preferably glycine is dissolved in deionized water.

In a preferred embodiment, glycine is dissolved in water to form a 20% (w/v) solution.

Preferably, glycine is dissolved at about room temperature. In some embodiments of the invention, the glycine solution is warmed up or cooled down to 20 or 21° C. In one embodiment, the temperature of the solution is adjusted to 20° C. In a further embodiment of the invention, the temperature of the solution is adjusted to 21° C.

After glycine is dissolved and, optionally, the temperature has been adjusted, acetone is added to precipitate the glycine. Preferably, the acetone is slowly added; more preferably, the acetone is added dropwise. The mixture is preferably stirred during the addition of acetone.

In a preferred embodiment, the addition of acetone is performed with temperature control. In a more preferred embodiment, the temperature of the mixture does not exceed 30° C. during the addition of acetone.

In one embodiment of the invention, an excess of acetone compared to the amount of glycine is added. In a preferred embodiment, at least 2 times the volume of acetone is added to the glycine solution, more preferably at least four time the volume of acetone is added to the glycine solution.

In some embodiments of the invention, the mixture is stirred further after the acetone is added.

Precipitated and recrystallized glycine is then collected and dried. In some embodiments, the precipitated glycine is washed with acetone, prior to drying. Preferably, the glycine is dried at room temperature. In some embodiments, the recrystallized glycine is air-dried at room temperature and at atmospheric pressure. In some embodiments, the recrystallized glycine is dried under vacuum.

After recrystallization, the glycine is combined with the acetyl salicylic acid lysinate obtained in step g). The glycine may be combined by mixing the compounds, preferably in solid form. It has been surprisingly found by the inventors, that the recrystallization step h) improves the mixing properties of the acetylsalicylic acid lysinate (or lysine acetylsalicylate) and the recrystallized glycine; for instance, improving homogeneity of the resulting mixture as well as preventing separation of the formed mixture (e.g. during subsequent processing operations such as filling into sachets or vials; or during storage). Without wishing to be bound by theory, it is currently believed that the improved mixing behavior is due to, or at least partially due to, the reduced density difference between the acetylsalicylic acid lysinate and the recrystallized glycine (as compared to glycine which has not been recrystallized prior to mixing).

In one embodiment, the solid compounds are mixed and stirred, preferably at room temperature. In a preferred embodiment, the compounds are mixed without applying additional heat. In a further preferred embodiment, the compounds are mixed at atmospheric pressure.

The last step (i.e. step i) allows to define the final LASAG composition. The amount of glycine in the final product (LASAG) can be easily controlled. In some embodiments, glycine is added in an amount of about 10 wt.-% of the amount of acetylsalicylic acid lysinate. In some embodiments the amount of glycine is about up to 20 wt.-% of the amount of acetylsalicylic acid lysinate.

After mixing, the lysine acetylsalicylate.glycine (LASAG) may further be prepared in any way needed. In some embodiments, the LASAG may be compressed into tablets; in alternative embodiments, the LASAG may be used in powdered form.

As mentioned above, the method is particularly suitable for producing LASAG particles with a defined particle size. Preferably, the LASAG particles obtained in step i) have a median particle size of less than 100 µm, preferably less than 80 µm, more preferably less than 50 µm, particularly preferably less than 40 µm and especially preferably less than 30 µm. In a further preferred embodiment, at least 90% of the LASAG particles obtained in step i) have a particle size of less than 200 µm, preferably less than 175 µm, more preferably less than then 150 µm, even more preferably less than 130 µm, particularly preferably less than 120 µm and especially preferably less than 110 µm. In a yet further preferred embodiment, not more than 10% of the LASAG particles obtained in step i) have a particle size of less than 1 µm, preferably less than 2 µm, more preferably less than 3 µm.

In a specific embodiment of the invention, the LASAG particles obtained in step i) have a median particle size of less than 50 µm and at least 90% of the particles have a particle size of 150 µm or less. In a preferred embodiment the LASAG particles obtained in step i) have a median particle size of less than 40 µm and at least 90% of the particles have a particle size of 130 µm or less. In a more preferred embodiment the LASAG particles obtained in step i) have a median particle size of less than 30 µm and at least 90% of the particles have a particle size of 110 µm or less.

The method steps a) to h) might be performed under sterile conditions. In this case, all used compounds should be sterile and suitable for pharmaceutical application. Alternatively, the method may not be performed under sterile conditions and the pharmaceutical product is sterilized subsequently in the optional step j). In a preferred embodiment the product is optionally sterilized in step j) using radiation.

An advantage of the method developed by the inventors is the temperature independence of the method. In contrast to other methods, the method is providing high yields in a short time at room temperature.

Within the context of the present invention room temperature refers to a temperature between 20° C. and 30° C. Preferably, room temperature refers to a temperature between 23° C. and 27° C. For example, room temperature may refer to a temperature of about 25° C.

In one particular embodiment of the invention, all method steps are performed at about the same temperature. Preferably, the method is performed at room temperature. In an alternative embodiment, the method is performed at or below room temperature, preferably at or below 20° C. In a further embodiment, the method is performed at or below a temperature of 15° C., preferably at or below 10° C., more preferably at or below 5° C. In one particular embodiment, the method is performed at or below 0° C.

In alternative embodiments, the method steps are performed at different temperatures. The method is working and providing significantly improved yields, even if single or multiple subsequent steps are performed at different temperatures.

In particular, steps a) and b) are completely independent of temperature. However, it is preferred that the solutions of step a) and/or b) are provided at or below room temperature, or are allowed to cool down to or below room temperature, prior to step c).

In one embodiment of the invention, the solutions of steps a) and/or b) are provided at room temperature. In an alternative embodiment of the invention the solutions of step a) and/or b) are provided below room temperature. In a preferred embodiment, the solutions of step a) and/or b) are provided at or below a temperature of about 20° C., preferably at or below a temperature of 15° C., more preferably at or below a temperature of 10° C., even more preferably at or below a temperature of 5° C. In a particular embodiment of the invention, the solutions of step a) and/or b) are provided at or below a temperature of 0° C.

Steps c) and d) of combining and optionally stirring the solutions are preferably performed at the same temperature, which at least one of the solutions of step a) or b) has. However, each of steps c) or d) might be performed at a different temperature. Preferably, steps c) and/or d) are performed at room temperature. In one embodiment, steps c) and/or d) performed at or below room temperature. In a particular embodiment of the invention, steps c) and/or d) are performed at or below 20° C., preferably at or below 15° C., more preferably at or below 10° C., even more preferably at or below 5° C. In one particular embodiment, steps c) and/or d) are performed at or below 0° C.

The addition of acetone in step e) is preferably performed at the same temperate as steps c) and d) or at the same temperature as the incubation step f). In one embodiment, step e) is performed at or below room temperature. In an alternative embodiment, step e) is performed at or below 20° C., preferably at or below 15° C., more preferably at or below 10° C., most preferably, at or below 5° C. In one particular embodiment step e) is performed at or below 0° C.

In one embodiment of the invention, the incubation step f) is performed at room temperature. In an alternative embodiment of the invention, the incubation step f) is performed at a temperature below room temperature. In a preferred alternative embodiment, the incubation step is performed at a temperature of at or below 20° C., more preferably at or below 15° C., even more preferably at or below 10° C. and most preferably at or below 5° C. In a particular alternative embodiment of the invention, the incubation step is performed at or below 0° C.

The isolation step g) and the optional washing step g1) are preferably performed at the same or a similar temperature as the incubation step. However, if a different temperature is used, the mixture and product may or may not adapt to the new temperature. For example, if step f) was performed at 5° C. and the isolation is performed at room temperature, the mixture containing the product may or may not warm up to room temperature before isolation.

Steps g) and h) might be performed at the same or different temperature. In a preferred embodiment, steps g) and/or h) are performed at or below room temperature. In an alternative embodiment, the steps g and/or h) are performed at or below 20° C., preferably at or below 15° C., more preferably at or below 10° C., most preferably at or below 5° C. In a particular embodiment, steps g) and/or h) are performed at or below 0° C.

The optional sterilization step may be performed at any suitable temperature.

EXAMPLES

Example 1: Preparation of Acetylsalicylic Acid Lysinate

Acetylsalicylic acid lysinate was prepared according to the reaction schematic shown in FIG. 1.

1 g of acetylsalicylic acid was dissolved in 11 mL of ethanol and 0.82 g of D,L-lysine monohydrate was dissolved in 2.5 mL of $H_2O$. The two solutions were mixed under stirring. After about 5 minutes white precipitate has formed. The suspension was further stirred for 30 minutes before 12 mL acetone were added and the mixture was further incubated.

The precipitate was collected by filtration, washed with acetone and analyzed by NMR and HPLC-MS. The yield was 1.429 g of acetylsalicylic acid lysinate (88%). A 7-fold scale up resulted in 91% yield.

Figure 2:
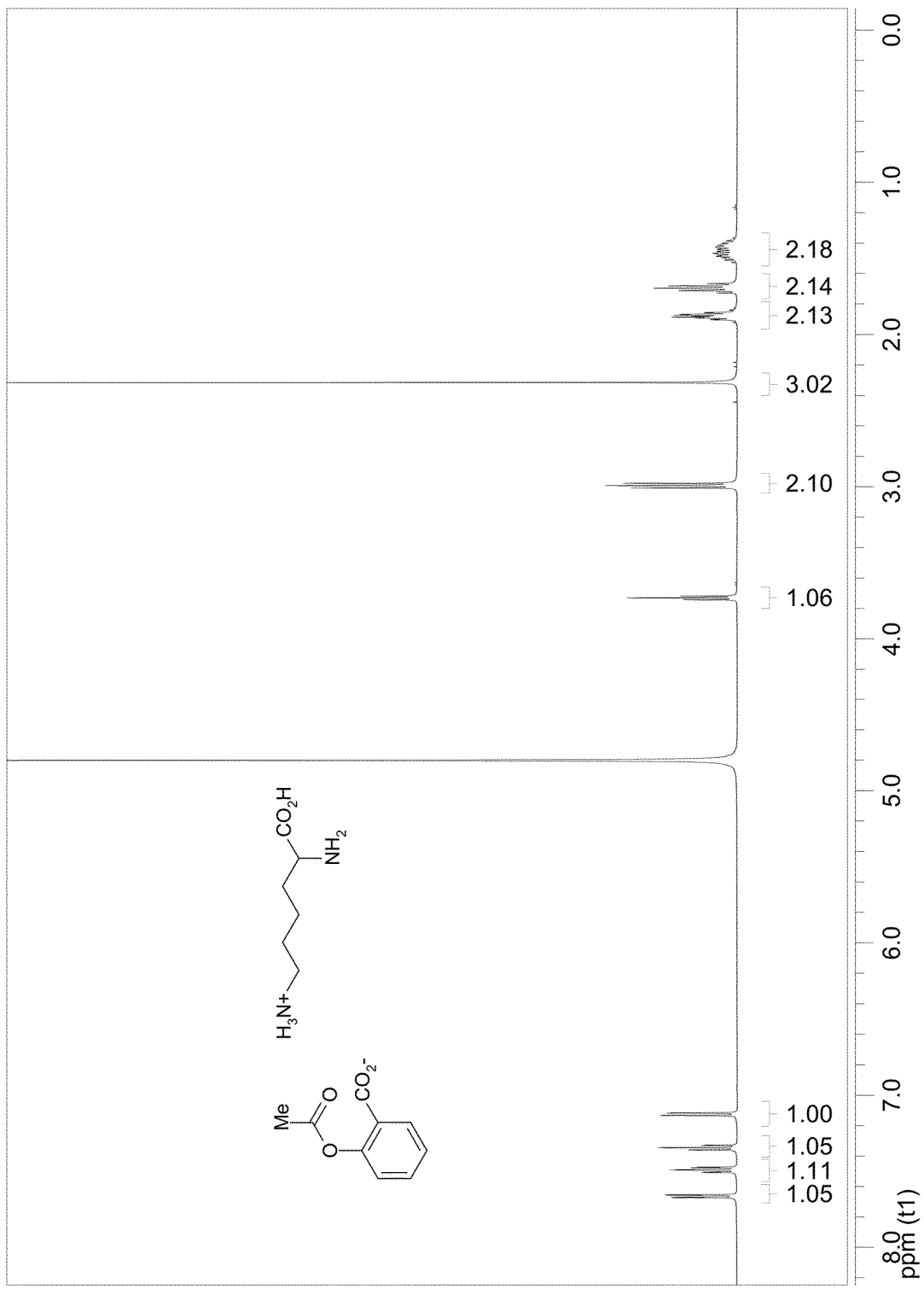
FIG. 2: 1H-NMR Analysis of acetylsalicylic acid lysinate generated with the method of the invention.

1H-NMR (D2O, 300 MHz, FIG. 2): δ=1.44 (br.m., 2H, —CH2-), 1.70 (br.m., 2H, —CH2-), 1.87 (br.m., 2H, —CH2-), 2.32 (s, 3H, Me), 3.00 (t, 2H, —CH2-, 3J=4.5 Hz), 3.73 (t, 2H, —CH2-, 3J=4.2 Hz), 7.12 (dd, 1H, H-3, 3J1=4.8 Hz, 3J2=0.6 Hz), 7.34 (dt, 1H, H-5, 3J1=4.5 Hz, 3J2=0.6 Hz), 7.49 (dt, 1H, H-4, 3J1=4.8 Hz, 3J2=0.9 Hz), 7.66 (dd, 1H, H-6, 3J1=4.8 Hz, 3J2=0.9 Hz).

Figure 3A:
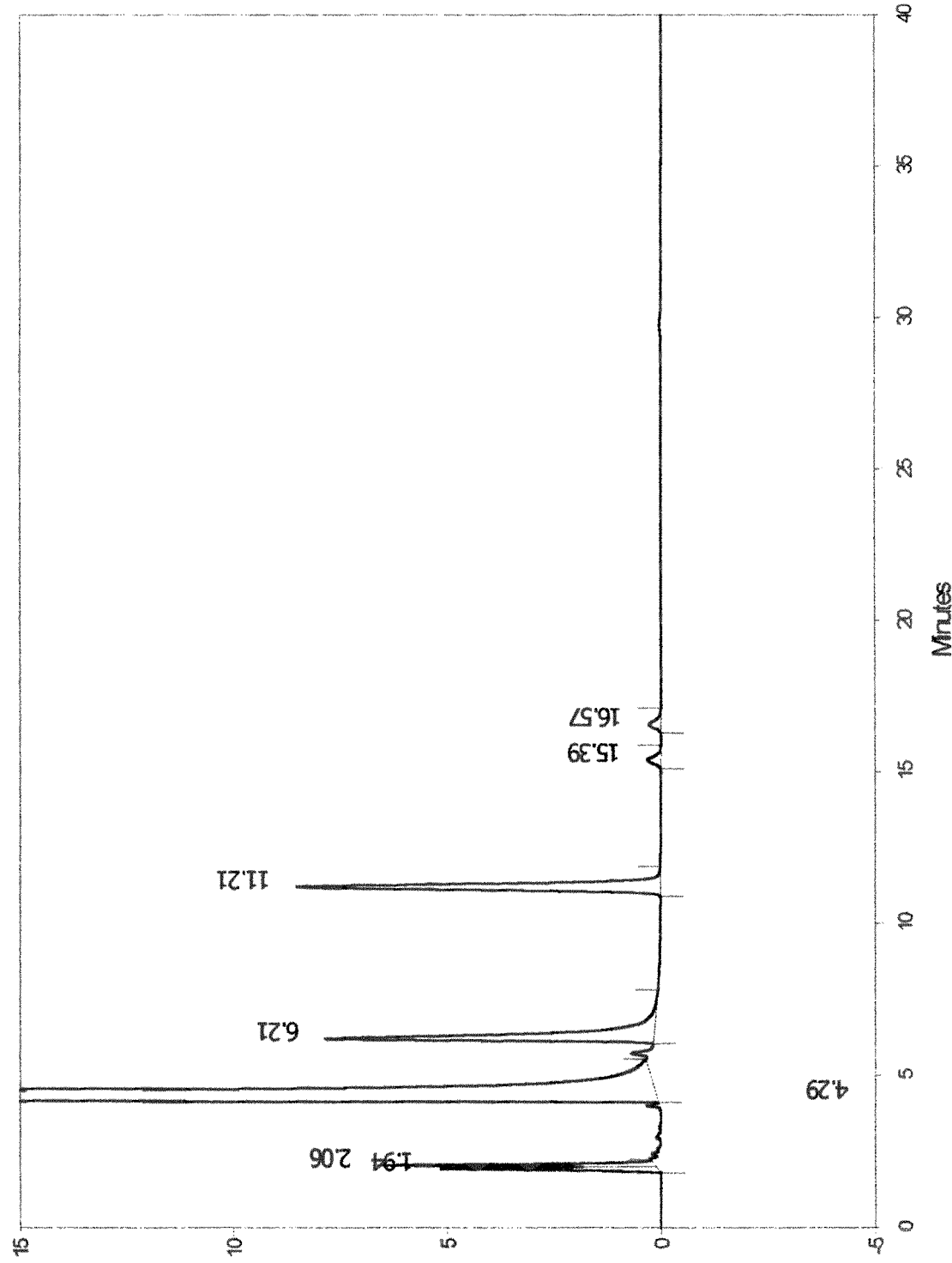
FIG. 3: HPLC-MS analysis of a) an acetylsalicylic acid lysinate sample produced according to the method of the invention and b) a sample of a commercially available acetylsalicylic acid lysinate sample.
Figure 3B:
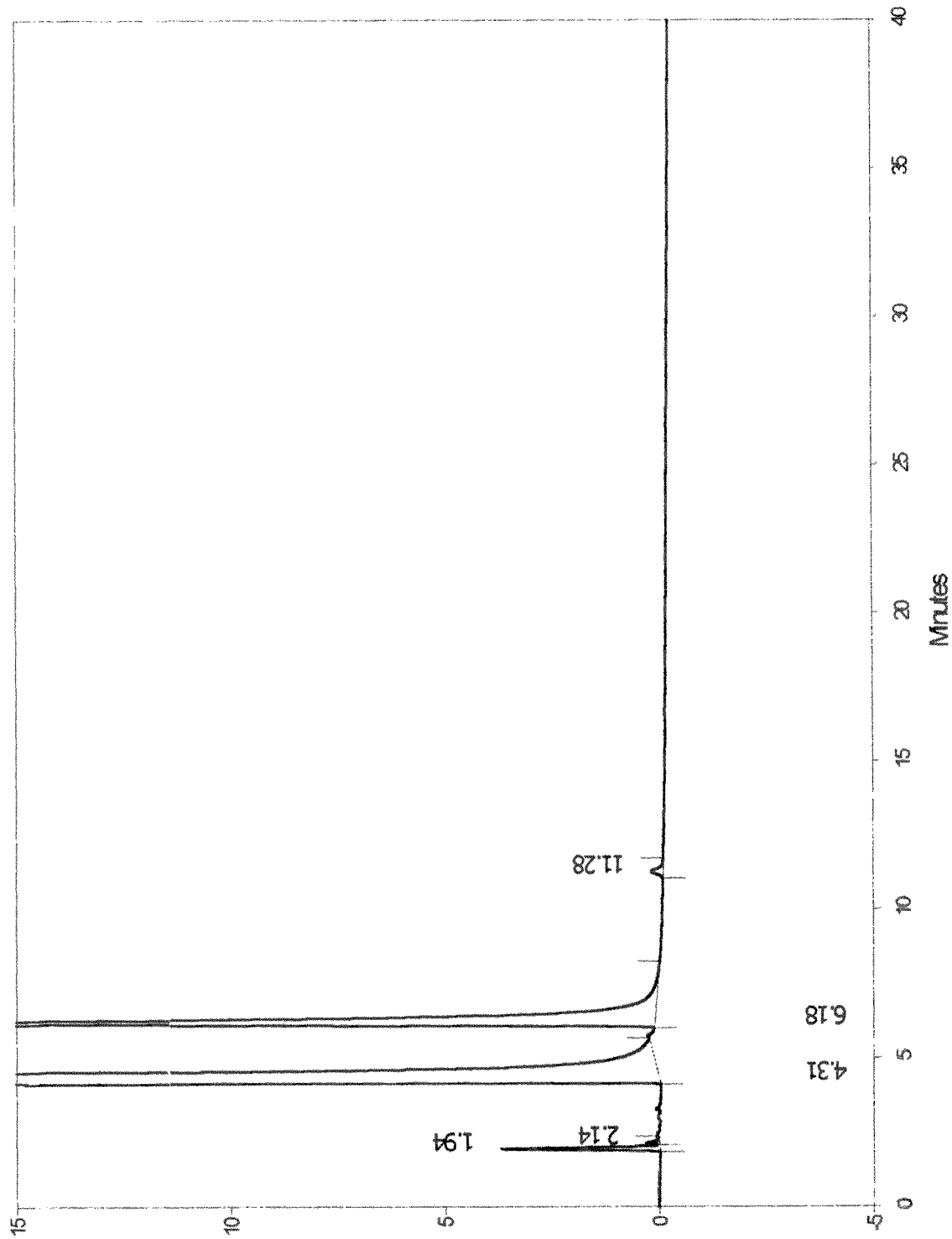

HPLC-MS analysis confirmed a purity comparable to commercially available products (FIGS. 3a and 3b).

Example 2: Preparation of Acetylsalicylic Acid Lysinate at Larger Batch Scale Acetylsalicylic acid lysinate was prepared according to the same reaction scheme as in Example 1, but at a larger batch scale.

135 grams of acetylsalicylic acid is mixed with 1.5 liters of ethanol. Upon The formation of a clear solution, 117.14 grams of D,L-lysine monohydrate dissolved in 340 mL of deionized water were rapidly added. A white precipitate is formed after 2 minutes. The suspension is kept stirring intensively. After 0.5 hours, 1.8 liters of acetone is added to the mixture and the stirring is continued for an additional 0.5 hour. The white precipitate is then filtered off, washed with 800 mL of acetone and dried on vacuum while heated to 45° C. with a water bath.

The yield was 222.62 g of acetylsalicylic acid lysinate (95%).

$^1$H-NMR ($D_2O$, 300 MHz): δ=1.44 (br.m., 2H, —$CH_2$—), 1.70 (br.m., 2H, —$CH_2$—), 1.87 (br.m., 2H, —$CH_2$—), 2.32 (s, 3H, Me), 3.00 (t, 2H, —$CH_2$—, $^3J$=4.5 Hz), 3.73 (t, 2H, —$CH_2$—, $^3J$=4.2 Hz), 7.12 (dd, 1H, H-3, $^3J_1$=4.8 Hz, $^3J_2$=0.6 Hz), 7.34 (dt, 1H, H-5, $^3J_1$=4.5 Hz, $^3J_2$=0.6 Hz), 7.49 (dt, 1H, H-4, $^3J_1$=4.8 Hz, $^3J_2$=0.9 Hz), 7.66 (dd, 1H, H-6, $^3J_1$=4.8 Hz, $^3J_2$=0.9 Hz).

Figure 4:
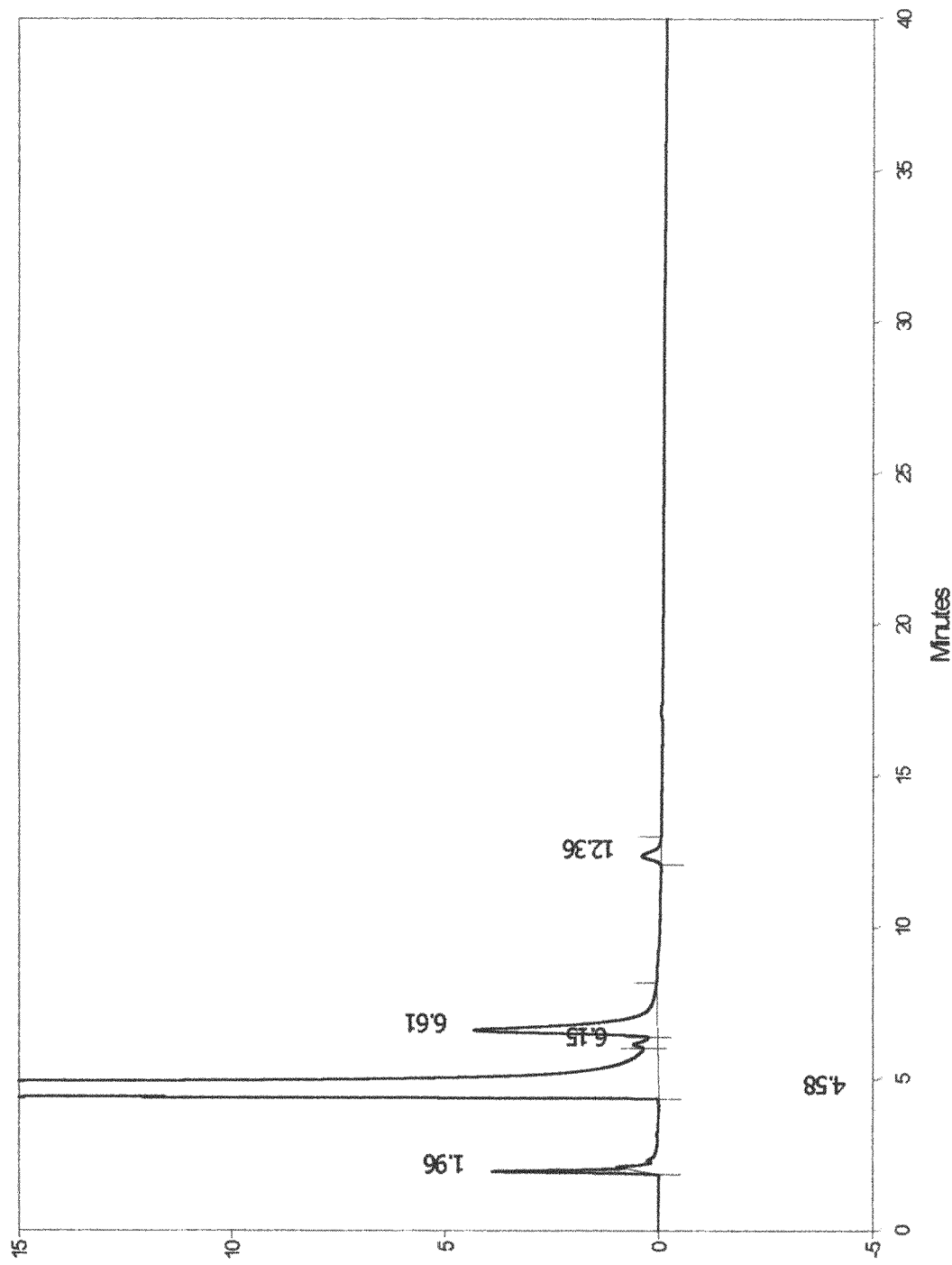
FIG. 4: HPLC-MS analysis of a) an acetylsalicylic acid lysinate sample produced according to the method of the invention in large scale.

HPLC-MS analysis confirmed a purity comparable to commercially available products (FIG. 4).

Example 3: Recrystallization of Glycine 10 grams of glycine were dissolved in 50 mL deionized water. The obtained solution was warmed up to 21° C., and subsequently 200 mL of acetone were added dropwise to the glycine solution under stirring. The acetone addition was performed with such speed that the temperature of the acetone/water mixture does not exceed 30° C. After the addition, the obtained suspension was further stirred for 60 minutes. The precipitate was then collected by filtration, washed with 30 mL of acetone and air-dried to give 9.29 g recrystallized glycine.

In an alternative example, 10 grams of glycine were dissolved in 50 mL deionized water. The obtained solution was warmed up to 20° C., and subsequently filtered off through porous glass filter. The filtrate was then added dropwise to 200 mL of acetone under stirring. The addition of aqueous solution was performed with such speed, that the temperature of the acetone/water mixture does not exceed 30° C. After the addition, the obtained suspension was further stirred for 20 minutes. The precipitate was collected by filtration, washed with 20 mL of acetone and air-dried to give 9.62 g recrystallized glycine.

Example 4: Preparation of Lysine Acetylsalicylate.Glycine (LASAG) Particles

Acetylsalicylic acid lysinate and recrystallized glycine were obtained as described above.

28.03 grams of acetylsalicylic acid lysinate and 2.80 grams of glycine were put into 500 mL round-bottom flask. The mixture was stirred on rotary evaporator without applied heat or reduced pressure for 1 hour 25 minutes to give the desired mixture. The amount of glycine in the resulting mixture is the range of 8 to 12 wt.-%.

Figure 5:
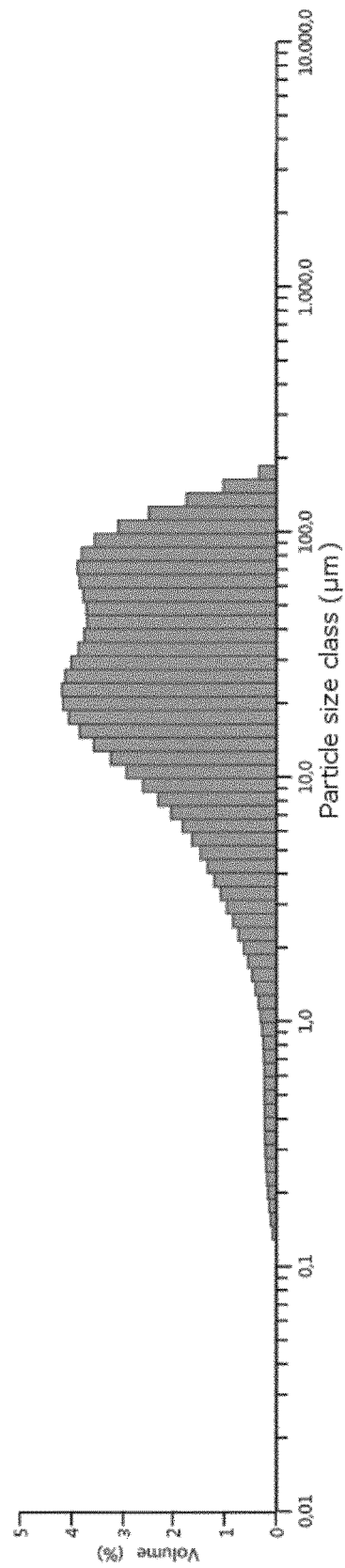
FIG. 5: Particle size distribution of a LASAG sample, produced according to the method of the invention.

FIG. 5 shows the particle size distribution (PSD) of a LASAG sample prepared with the method according to the invention. The particle size was measured using laser diffraction, here specifically using the Mastersizer 3000 laser diffractometer (Malvern Instruments) equipped with a dry powder module. It can be seen that the majority of particles has a particle size of less than 100 μm, with only about 5.5 vol.-% of the particles showing a particle size above 100 μm.

The particle size distribution (PSD) of the particles is also shown in the table below:

| Size (μm) | % volume |
|---|---|
| 0.0100 | 0.00 |
| 0.0114 | 0.00 |
| 0.0129 | 0.00 |
| 0.0147 | 0.00 |
| 0.0167 | 0.00 |
| 0.0189 | 0.00 |
| 0.0215 | 0.00 |
| 0.0244 | 0.00 |
| 0.0278 | 0.00 |
| 0.0315 | 0.00 |
| 0.0358 | 0.00 |
| 0.0407 | 0.00 |
| 0.0463 | 0.00 |
| 0.0526 | 0.00 |
| 0.0597 | 0.00 |
| 0.0679 | 0.00 |
| 0.0771 | 0.00 |
| 0.0876 | 0.00 |
| 0.0995 | 0.00 |
| 0.113 | 0.00 |
| 0.128 | 0.06 |
| 0.146 | 0.10 |
| 0.166 | 0.12 |
| 0.188 | 0.15 |
| 0.214 | 0.17 |
| 0.243 | 0.19 |
| 0.276 | 0.20 |
| 0.314 | 0.21 |
| 0.357 | 0.21 |
| 0.405 | 0.22 |
| 0.460 | 0.22 |
| 0.523 | 0.22 |
| 0.594 | 0.22 |
| 0.675 | 0.23 |
| 0.767 | 0.24 |
| 0.872 | 0.26 |
| 0.991 | 0.29 |
| 1.13 | 0.34 |
| 1.28 | 0.39 |
| 1.45 | 0.46 |
| 1.65 | 0.53 |
| 1.88 | 0.62 |
| 2.13 | 0.72 |
| 2.42 | 0.83 |
| 2.75 | 0.95 |
| 3.12 | 1.07 |
| 3.55 | 1.19 |
| 4.03 | 1.32 |
| 4.58 | 1.46 |
| 5.21 | 1.62 |
| 5.92 | 1.81 |
| 6.72 | 2.03 |
| 7.64 | 2.28 |
| 8.68 | 2.58 |
| 9.86 | 2.90 |
| 11.2 | 3.23 |
| 12.7 | 3.56 |
| 14.5 | 3.84 |
| 16.4 | 4.05 |
| 18.7 | 4.16 |
| 21.2 | 4.18 |
| 24.1 | 4.12 |
| 27.4 | 4.00 |
| 31.1 | 3.86 |
| 35.3 | 3.75 |
| 40.1 | 3.69 |
| 45.6 | 3.70 |
| 51.8 | 3.76 |
| 58.9 | 3.84 |
| 66.9 | 3.88 |
| 76.0 | 3.80 |
| 86.4 | 3.54 |
| 98.1 | 3.09 |
| 111 | 2.46 |
| 127 | 1.73 |
| 144 | 1.01 |
| 163 | 0.32 |
| 186 | 0.00 |
| 211 | 0.00 |
| 240 | 0.00 |
| 272 | 0.00 |
| 310 | 0.00 |
| 352 | 0.00 |
| 400 | 0.00 |
| 454 | 0.00 |
| 516 | 0.00 |
| 586 | 0.00 |
| 666 | 0.00 |
| 756 | 0.00 |
| 859 | 0.00 |
| 976 | 0.00 |
| 1110 | 0.00 |
| 1260 | 0.00 |
| 1430 | 0.00 |
| 1630 | 0.00 |
| 1850 | 0.00 |
| 2100 | 0.00 |
| 2390 | 0.00 |
| 2710 | 0.00 |
| 3080 | 0.00 |
| 3500 | |

The median particle size measured for this LASAG sample is 24.5 μm, and 90% of the particles have a particle size of 93.3 μm or less (i.e. Dv(90)=93.3 μm).

The invention claimed is:
1. A method for the production of lysine acetylsalicylate.glycine comprising the steps:
   a) providing a solution of acetylsalicylic acid in ethanol;
   b) providing an aqueous solution of lysine;
   c) combining the solutions of step a) and b) to form a mixture;
   d) optionally stirring the mixture;
   e) adding acetone to the mixture;
   f) incubating the mixture, to allow the formation of a acetylsalicylic acid lysinate product;
   g) isolating the acetylsalicylic acid lysinate product;
   wherein acetylsalicylic acid is used in excess compared to lysine and
   wherein no seed crystals are added to the mixture;
   h) providing a recrystallized glycine; wherein the glycine has been recrystallized with the following steps:
   h1) dissolving glycine in water;
   h2) adding acetone to the glycine solution;
   h3) stirring the mixture until a precipitate is obtained;
   i) combining the recrystallized glycine of step h) with the acetylsalicylic acid lysinate product of step g) to obtain lysine acetylsalicylate.glycine (LASAG) particles.

2. The method according to claim 1, wherein the particles obtained in step i) have a median particle size of less than 40 μm, and wherein at least 90% of the particles obtained in step i) have a particle size of less than 110 μm.

3. The method according to claim 1, wherein at least method steps c) to f) and/or h) and i) are performed at room temperature or below.

4. The method according to claim 1, wherein the incubation step f) is performed at 10° C. or less.

5. The method according to claim 1, wherein the isolation in step g) is performed by filtration.

6. The method according to claim 1, wherein the isolation in step g) is performed by centrifugation.

7. The method according to claim 1, wherein the solution of acetylsalicylic acid provided in step a) comprises about 8 to 12% (w/v), preferably about 9 to 10% (w/v) acetylsalicylic acid.

8. The method according to claim 1, wherein the aqueous solution of lysine provided in step b) comprises about 30 to 35% (w/v) lysine.

9. The method according to claim 1, wherein the aqueous solution of lysine provided in step b) further comprises dissolved glycine, and wherein the concentration of the glycine in the solution is optionally from 2 to 20% (w/v).

10. The method according to claim 1, wherein the aqueous solution of lysine provided in step b) was prepared from lysine monohydrate.

11. The method according to claim 1, wherein acetylsalicylic acid and lysine are used at a molar ratio of 1 to 0.9, or at a ratio of 1 to 0.95.

12. The method according to claim 1, additionally comprising the step:
 g1) washing the isolated product.

13. The method according to claim 12, wherein the washing step involves washing the product with acetone.

14. The method according to claim 1, wherein the method is performed under sterile conditions.

15. The method according to claim 1, wherein the method is performed under non-sterile conditions and comprises the additional step:
 j) sterilizing the product by irradiation.

16. A lysine acetylsalicylate.glycine obtainable by a method according to claim 1, wherein the lysine acetylsalicylate.glycine particles have a median particle size of less than 100 μm.

17. The lysine acetylsalicylate.glycine according to claim 16, wherein the lysine acetylsalicylate.glycine particles have a median particle size of less than 80 μm.

18. The lysine acetylsalicylate.glycine according to claim 16, wherein the lysine acetylsalicylate.glycine particles have a median particle size of less than 50 μm.

* * * * *

UNITED STATES PATENT AND TRADEMARK OFFICE
CERTIFICATE OF CORRECTION

PATENT NO. : 10,882,811 B2
APPLICATION NO. : 16/472726
DATED : January 5, 2021
INVENTOR(S) : Karlheinz Nocker et al.

Page 1 of 2

It is certified that error appears in the above-identified patent and that said Letters Patent is hereby corrected as shown below:

On the Title Page

Item (54) and in the Specification, Column 1, Lines 1-3, In the Title, "LYSINE ACETYLSALICYLATE GLYCINE" should be changed to -- LYSINE ACETYLSALICYLATE·GLYCINE --

Item (57), Abstract, Lines 2-3, "lysine acetylsalicylate.glycine" should be changed to -- lysine acetylsalicylate·glycine --

Item (57), Abstract, Line 19, "lysine acetylsalicylate.glycine" should be changed to -- lysine acetylsalicylate·glycine --

In the Specification

In Column 1, Line 38, "lysine acetylsalicylate.glycine" should be changed to -- lysine acetylsalicylate·glycine --

In Column 1, Lines 39-40, "lysine acetylsalicylate.glycine" should be changed to -- lysine acetylsalicylate·glycine --

In Column 1, Lines 66-67, "lysine acetylsalicylate.glycine" should be changed to -- lysine acetylsalicylate·glycine --

In Column 2, Line 20, "lysine acetylsalicylate.glycine" should be changed to -- lysine acetylsalicylate·glycine --

In Column 2, Line 50, "lysine acetylsalicylate.glycine" should be changed to -- lysine acetylsalicylate·glycine --

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,882,811 B2

In Column 2, Line 54, "lysine acetylsalicylate.glycine" should be changed to -- lysine acetylsalicylate·glycine --

In Column 3, Line 9, "lysine acetylsalicylate.glycine" should be changed to -- lysine acetylsalicylate·glycine --

In Column 3, Lines 14-15, "lysine acetylsalicylate.glycine" should be changed to -- lysine acetylsalicylate·glycine --

In Column 6, Lines 38-39, "lysine acetylsalicylate.glycine" should be changed to -- lysine acetylsalicylate·glycine --

In Column 7, Line 37, "lysine acetylsalicylate.glycine" should be changed to -- lysine acetylsalicylate·glycine --

In Column 10, Lines 46-47, "lysine acetylsalicylate.glycine" should be changed to -- lysine acetylsalicylate·glycine --

In the Claims

In Claim 1, Column 12, Lines 29-30, "lysine acetylsalicylate.glycine" should be changed to -- lysine acetylsalicylate·glycine --

In Claim 16, Column 14, Line 7, "lysine acetylsalicylate.glycine" should be changed to -- lysine acetylsalicylate·glycine --

In Claim 16, Column 14, Lines 8-9, "lysine acetylsalicylate.glycine" should be changed to -- lysine acetylsalicylate·glycine --

In Claim 17, Column 14, Line 11, "lysine acetylsalicylate.glycine" should be changed to -- lysine acetylsalicylate·glycine --

In Claim 17, Column 14, Line 12, "lysine acetylsalicylate.glycine" should be changed to -- lysine acetylsalicylate·glycine --

In Claim 18, Column 14, Line 14, "lysine acetylsalicylate.glycine" should be changed to -- lysine acetylsalicylate·glycine --

In Claim 18, Column 14, Line 15, "lysine acetylsalicylate.glycine" should be changed to -- lysine acetylsalicylate·glycine --